United States Patent [19]

Kozacik

[11] Patent Number: 4,521,377
[45] Date of Patent: Jun. 4, 1985

[54] FLOW THROUGH GAS ANALYZER

[76] Inventor: John J. Kozacik, 1116 Carney St., Cincinnati, Ohio 45239

[21] Appl. No.: 352,213

[22] Filed: Feb. 25, 1982

[51] Int. Cl.³ ............................................. G01N 7/00
[52] U.S. Cl. ...................................... 422/92; 73/149;
422/100
[58] Field of Search .................. 436/148; 422/92, 100;
73/23, 149

[56] References Cited

U.S. PATENT DOCUMENTS 2,363,027 11/1944 Vayda et al. ......................... 422/92
2,866,691 12/1958 Feichtinger ......................... 436/148
4,299,794 11/1981 Kelley et al. ........................ 436/148

Primary Examiner—Hiram H. Bernstein
Attorney, Agent, or Firm—Frost & Jacobs

[57] ABSTRACT

A flow through fluid analyzer and method of analysis which comprises providing a transparent analyzer tube having an open ended outer reservoir, a capillary tube connected at one end to the inner end of the outer reservoir and at its opposite end to the inner end of an inner reservoir provided with means for drawing fluid placed in the outer reservoir through the capillary tube into the inner reservoir and for returning the fluid to the outer reservoir, the analyzer being first filled with a carrier fluid which is nonreactive or predictably reactive to the constituents of the fluid being analyzed, followed by the introduction of a sample bubble of the fluid to be analyzed into the outer reservoir, the volume of the sample bubble being initially measured as it is drawn through the capillary tube into the inner reservoir by measuring the change in the volume of fluid in the inner reservoir as the leading and trailing ends of the sample bubble pass a reference point on the capillary tube. The carrier fluid is replaced by a reagent for a constituent of the sample bubble and the reagent reacted with the sample, followed by return of the bubble to the capillary tube where its volume is again measured, the difference in volume of the sample bubble between the first and second measurements indicating the volume of the constituent affected by the reagent. If additional constituents of the sample are to be measured, the first reagent is replaced by a reagent for another constituent of the sample bubble and the procedure repeated.

10 Claims, 4 Drawing Figures

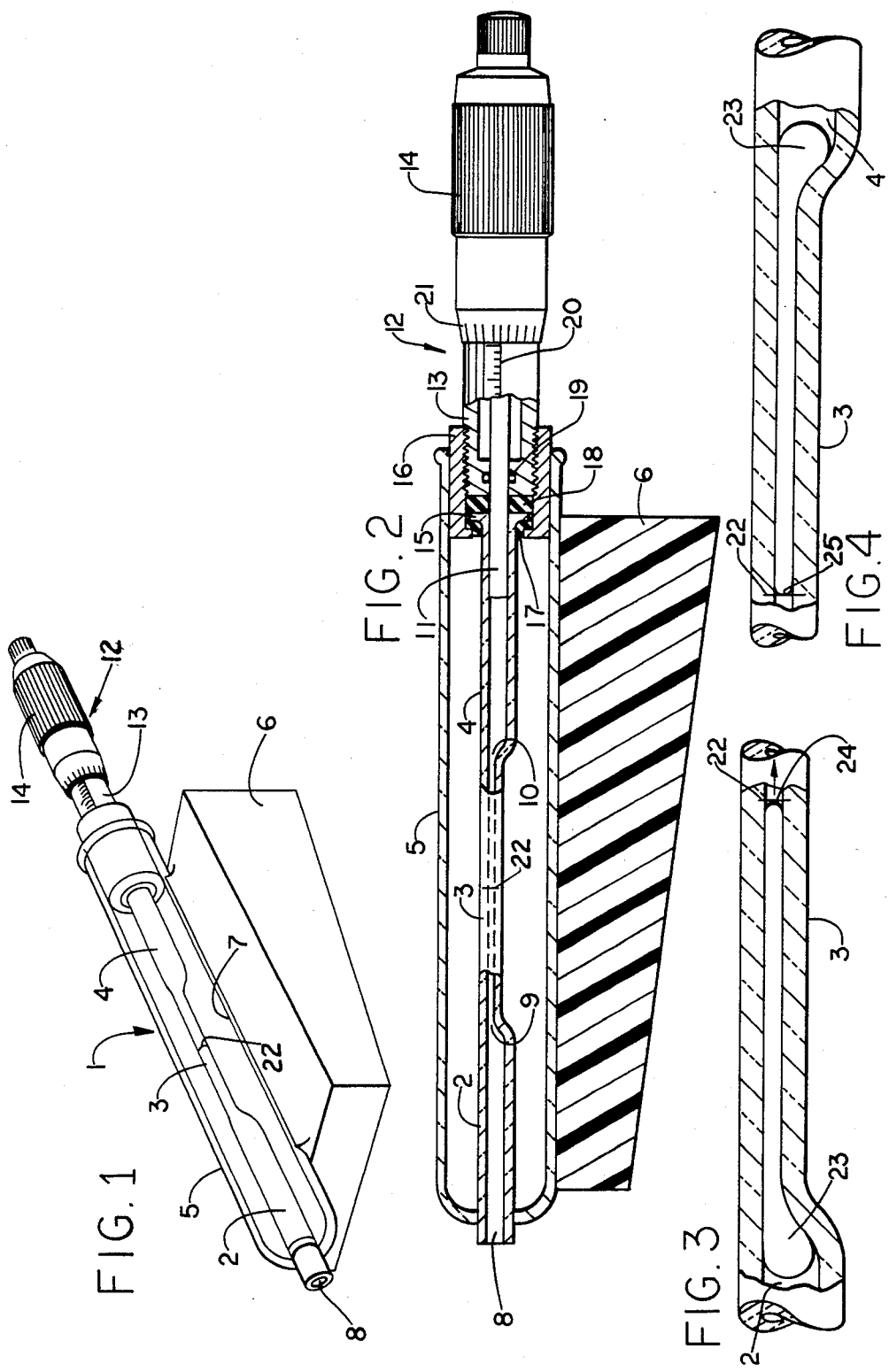

FLOW THROUGH GAS ANALYZER

This invention relates to the measurement of the concentrations of the constituent gases contained in a gas sample composed of a mixture of gases.

BACKGROUND OF THE INVENTION

Various devices and techniques have hitherto been proposed to measure the concentration of gases in a given sample, but such devices in general are of complicated construction and hence expensive to manufacture. Due to their complexity, they are difficult to use and require considerable expertise on the part of the person conducting the analysis. In addition, many of these devices require relatively large gas samples in order to obtain accurate readings, and in many instances a separate sample must be used for each different gas being measured.

Despite the number and variety of devices currently available which measure the concentration of gases in a given gas sample, there is no simple and inexpensive device which can be used for such a measurement with a minimum of training and expertise and yet provides a high degree of accuracy. In particular, there is a great need for a simple and inexpensive analyzer which can be used in the classroom as well as for chemical and research applications. The present invention fills this void by providing a micro fluid analyzer and method of analysis which operates solely by chemical-mechanical means and yet provides a high degree of accuracy and the ability to conduct the desired analysis in a relatively short period of time.

SUMMARY OF THE INVENTION

A basic flow-through micro fluid analyzer in accordance with the present invention comprises an elongated tubular member, preferably formed from glass, having a pair of reservoirs interconnected by a capillary tube. The first or outer reservoir has an open end through which the various reagents and samples to be analyzed are introduced. The second or inner reservoir is sealingly connected to a micrometer assembly having a body provided with a rotatable head and a plunger adapted, by movement within the inner reservoir, to decrease the volume of the inner reservoir upon rotation of the head in one direction, rotation of the head in the opposite direction acting to increase the volume of the inner reservoir. Calibrated indicia is provided on the micrometer head to measure the change in the volume of the inner reservoir as the plunger is moved within the inner reservoir.

The capillary tube is provided intermediate its ends with a reference mark which is utilized in conjunction with the calibrated indicia to measure the volume of the sample bubble being analyzed. The volume of the sample is measured as it passes through the capillary tube, the capillary tube acting to increase the resolution of the measurement by precisely defining the menisci of the sample.

In using the device, it is first filled with a carrier solution in which the gases being analyzed will not dissolve. This is accomplished by turning the head of the micrometer assembly until the plunger is fully inserted in the inner reservoir. The device is then tilted to a position in which the outer reservoir is uppermost, whereupon the outer reservoir is filled with the carrier solution and the solution drawn through the capillary tube into the inner reservoir by displacing the plunger within the inner reservoir. Additional carrier solution will be introduced into the outer reservoir and the process repeated until the analyzer is completely filled with carrier solution.

The gas sample to be analyzed is then injected into the carrier solution in the outer chamber by means of a syringe while the analyzer is tilted so that the inner reservoir is uppermost. By tapping the analyzer the sample bubble will float to the outer mouth of the capillary tube. The sample bubble is then drawn into and eventually through the capillary tube into the inner reservoir by displacing the plunger. The initial volume of the sample bubble is measured while the sample bubble is drawn through the capillary tube by taking readings from the calibrated indicia on the micrometer assembly, a first reading being taken when the leading end or leading meniscus of the sample bubble coincides with the reference mark on the capillary tube, a second reading being taken when the trailing end or trailing meiniscus of the sample bubble coincides with the reference mark. The difference between these two readings provides a precise measurement of the volume of the sample.

When the sample bubble has been completely drawn into the inner reservoir, the analyzer is gently tapped to cause the sample bubble to float toward the plunger in the inner reservoir. The plunger is then moved inwardly, thereby decreasing the volume of the inner reservoir and forcing carrier fluid from the inner reservoir, the carrier fluid flowing through the capillary tube into the outer reservoir where it may be removed using a syringe. At this point the inner reservoir contains only a small amount of the carrier fluid and the sample bubble. A reagent to be reacted with the sample bubble is then introduced into the now empty outer reservoir and drawn through the capillary tube into the inner reservoir as the plunger is again moved to increase the volume of the inner reservoir. When the inner reservoir is filled with the reagent, reaction with the sample bubble may be facilitated by tilting and gently shaking the analyzer so as to move the sample bubble back and forth within the inner reservoir. After allowing sufficient time for the reagent to react with the sample bubble, the analyzer is tilted so as to cause the sample bubble to move to the inner mouth of the capillary tube. The sample bubble is then caused to pass through the capillary tube where its volume is again measured as its leading and trailing ends pass the reference mark in the capillary tube using the calibrated indicia on the micrometer assembly. Following measurement, the sample bubble will be returned to the inner reservoir, followed by the removal of the first reagent in the same manner as the carrier solution, whereupon, if desired, additional reagents may be introduced in like manner to measure additional constituents of the sample bubble.

DESCRIPTION OF THE DRAWINGS

FIG. 1 is a perspective view of a fluid analyzer in accordance with the invention.

FIG. 2 is a vertical sectional view of the analyzer.

FIG. 3 is an enlarged fragmentary sectional view of a sample bubble as its leading end enters the capillary tube.

FIG. 4 is an enlarged fragmentary sectional view of a sample bubble as its trailing end passes through the capillary tube.

DESCRIPTION OF THE PREFERRED EMBODIMENT

Referring first to FIG. 1, the gas analyzer comprises an elongated tubular member defining an outer reservoir 2, a capillary tube 3, and an inner reservoir 4, preferably formed from glass, although plastic materials may be used provided they are inert with respect to the materials being handled. It is preferred that the capillary tube and the reservoirs have their top inner wall surfaces lying in a common plane to facilitate manipulation of the samples being analyzed. In the embodiment illustrated, the analyzer tube is surrounded by a protective transparent jacket 5 which may be filled with water or other fluid medium effective to insulate the analyzer tube. To facilitate the handling of the device, the jacket 5 may be seated on an inclined platform 6 having a seat 7 to receive the jacket. The platform will provide a shallow angle of tilt, which may be on the order of 5–10 degrees from the horizontal, thereby permitting the analyzer to be positioned with either end lowermost.

The outer reservoir 2 has an open end 8 through which the carrier solution, the sample, and the various reagents are introduced, the outer reservoir terminating at its inner end in a narrow neck 9 defining the outer mouth of the capillary tube 3. Similarly, the inner end of the inner reservoir 4 terminates in a narrow neck 10 defining the inner mouth of the capillary tube. The reservoirs 2 and 4 are of generally cylindrical configuration and of a size to receive and hold the desired quantities of fluid. Their size may vary depending upon the intended use of the analyzer, as will the size of the capillary tube 3.

In accordance with the invention, means are provided in association with the inner reservoir 4 to draw fluid into the inner reservoir through the capillary tube 3 and to return the fluid through the capillary tube to the outer reservoir 2. In the embodiment shown, this is accomplished by a plunger 11 slidably fitted within the inner reservoir 4, the plunger acting as a piston and forming a part of the micrometer assembly 12, which is of known construction. The micrometer assembly comprises a cylindrical body 13 having a rotatable head 14 adapted, upon rotation, to axially displace the plunger 11, the plunger moving inwardly within the inner reservoir when the head is rotated in one direction, and moving outwardly within the reservoir when the head is rotated in the opposite direction. The micrometer assembly is attached to the flared end 15 of the inner reservoir 4 by means of a threaded collar 16 acting in conjunction with gaskets 17 and 18, and O-ring 19, thereby assuring a tight seal between the micrometer body, the analyzer tube and the plunger. Calibrated indicia 20 and 21 on the body 13 and rotatable head 14, respectively, provide a precise measurement of plunger displacement which is linearly related to volumetric change. For example, the indicia 20 on the body may provide a linear scale which can be utilized to indicate volume changes up to 200 uL in divisions of 10 uL, whereas the indicia 21 on the rotatable head may provide a circular scale to indicate volume changes of 10 uL in divisions of 0.2 uL.

The scales 20 and 21 are utilized in conjunction with a reference mark 22 on the capillary tube 3 to measure the volume of the sample bubble during its analysis. Thus, as seen in FIG. 3, as a sample bubble 23 is drawn through the capillary tube 3 toward the inner reservoir 4, a first reading of the indicia 20 and 21 will be taken when the leading end 24 of the bubble 23 coincides with the reference mark 22. A second reading is taken when the trailing end 25 of the bubble 23 coincides with the reference mark 22, as seen in FIG. 4, and the difference between the two readings will give a precise measurement of the volume of the bubble 23.

A flow through fluid analyzer in accordance with the invention can be utilized to determine the concentration of any constituent in any mixture of gases, provided there is a relatively inert or predictably reactive carrier for the mixture and also a liquid reactant for each constituent gas of interest which is compatible with the carrier. The analyzer also may be used for liquids where the sample being analyzed is immiscible with the carrier solution and the reactants. In all instances, the first step is to sequester the sample bubble in a carrier solution, measure the volume of the sample as it passes through the capillary tube, then replace the carrier solution with a reagent which reacts with the constituent of interest, followed by the remeasuring of the volume of the sample. The change in volume divided by the original volume of the sample multipled by 100 gives the percentage concentration of the constituent being measured.

By way of a nonlimiting example of the use of the analyzer, it may be used to measure respiratory gas samples for their content of carbon dioxide, oxygen, and nitrogen. The carbon dioxide will be absorbed by potassium hydroxide, and oxygen by a chemical composition known as pyrogallol. While the nitrogen constituent is actually a mixture of nitrogen and the noble gases, since the amount of the noble gases is exceedingly small, the remainder is referred to as nitrogen.

In conducting the analysis, the analyzer is first filled with a carrier solution in which the respiratory gases will not dissolve. An acid rinse solution of the following composition may be used:
400 ml. distilled water
1 ml. concentrated sulfuric acid
72 gr. anhydrous sodium sulfate
21 ml. glycerol
320 m. gr. sodium or potassium dichromite.

After thorough cleaning, the analyzer is filled with the acid rinse solution, the plunger 11 being first moved to its innermost position by turning rotatable head 14, and the outer reservoir 2 filled with the solution, the analyzer being held in a tilted position with the outer reservoir 2 uppermost. The plunger 11 is then retracted to draw the solution through the capillary tube into the inner reservoir 4. When the solution has been drawn into the inner reservoir 4, gentle tapping of the analyzer, while maintained in its tilted position, will cause any entrained air bubbles to rise to the inner mouth 10 of the capillary tube, the entrained air bubbles being expelled by turning rotatable head 14 to cause the plunger 11 to move inwardly within inner reservoir 4. Additional rinse solution will be introduced into the outer reservoir 2 and the procedure repeated until the analyzer is completely filled with the rinse solution and the plunger is at least partially contained within the inner reservoir 4.

The respiratory gas sample is then injected into the rinse solution in the outer reservoir 2 by means of a syringe with the analyzer tilted so that the outer reservoir 2 is lower, i.e., in the position illustrated in FIG. 1. By again tapping the analyzer the sample bubble of gas will float to the outer mouth 9 of the capillary tube 3, whereupon the bubble is drawn through capillary tube 3 by moving plunger 11 outwardly within inner reservoir 4.

The volume of the sample bubble is measured as it passes through the capillary tube 3, using the calibrations 20 and 21 on the micrometer assembly 12 and reference mark 22 on the capillary tube to make the measurement. When the sample bubble is completely drawn within the inner reservoir 4, and the analyzer tilted so that the inner reservoir is uppermost, by again gently tapping the analyzer the bubble will float to the plunger end of the inner reservoir. The plunger 11 is then moved inwardly within reservoir 4 to force the bulk of the rinse solution from inner reservoir, the solution returning to the outer reservoir 2 where it is removed by a syringe.

A carbon dioxide absorber, which may comprise a solution of 100 ml. distilled water, 11 gr. potassium hydroxide, and 40 m. gr. sodium or potassium dicromate, is then introduced into the outer reservoir 2 and drawn through the capillary tube 3 into the inner reservoir 4 as the plunger 11 is again moved outwardly within the inner reservoir, the inner reservoir being filled with the reagent. Absorption of the carbon dioxide in the sample bubble is facilitated by tilting and gently shaking the analyzer so as to move the sample bubble back and forth within inner reservoir 4. After allowing sufficient time for the potassium hydroxide solution to react with the carbon dioxide in the sample bubble, the analyzer is tilted so as to place the inner reservoir 4 lowermost, thereby causing the sample bubble to move to the inner mouth 10 of the capillary tube 3. The plunger is again moved inwardly to cause the bubble to pass through the capillary tube, preferably into the outer reservoir. With sufficient reagent in the outer reservoir and a shallow angle of tilt, the sample bubble will be maintained by surface tension at the outer mouth of the capillary tube and will not escape from the outer reservoir. Thereafter the analyzer is fitted so as to place the outer reservoir 2 lowermost and the sample bubble is returned to the inner reservoir 3, its volume being measured as it passes the reference mark 22 and the concentration of carbon dioxide in the sample bubble determined by the formula:

$$\% CO_2 = \frac{\text{Initial volume} - \text{Volume after KOH}}{\text{Initial volume}} \times 100$$

While the volume of the bubble may be measured as it moves through the capillary tube in either direction, it is preferred to move the bubble into the outer reservoir 2 and then return it to the capillary tube 3. By maintaining the outer reservoir completely filled with fluid and following this procedure, the possible inclusion of a stray air bubble is avoided.

Upon return of the sample bubble to the inner reservoir 4, the analyzer is then manipulated to place the sample bubble at the plunger end of the inner reservoir 4 and the potassium hydroxide solution discharged in the same manner as the rinse solution. The discharged carbon dioxide absorber is replaced by an absorber for oxygen, which may comprise a solution prepared by placing 15 gr. pyrogallol in a 250 ml. Mariotte bottle, covering the pyrogallol with 100 ml. parafin oil and adding 100 ml. of a 20% aqueous solution of sodium hydroxide, the pyrogallol being disolved in the solution by gentle stirring.

This solution is introduced into the outer reservoir 2 and drawn into the inner reservoir 4 where it is reacted with the sample bubble in the same manner as the carbon dioxide absorber, followed by the return of the sample bubble to the capillary tube 3 where its volume is again measured using the reference mark 22, the concentration of oxygen being determined by the formula:

$$\% O_2 = \frac{\text{Volume after KOH} - \text{Volume after pyrogallol}}{\text{Initial volume}} \times 100$$

The nitrogen content of the sample is then determined by the formula:

$$\% N_2 = \frac{\text{Volume after pyrogallol}}{\text{Initial volume}} \times 100$$

In practicing the invention, care must be taken to insure that the analyzer is clean, otherwise the reagents will not wet the walls of the reservoirs and capillary tube and difficulty will be experiences in manipulating the sample bubble. Care should also be taken to draw the sample bubble through the capillary tube slowly and smoothly to avoid the formation of droplets of the solutions on the inner surfaces of the analyzer.

As should now be evident, the present invention provides a simple and inexpensive micro fluid analyzer which can be readily manipulated to provide an accurate volumetric analysis of the constituents of a sample being analyzed. An essential feature of the invention resides in the measurement of the sample as it passes through the capillary tube, such procedure providing enhanced resolution and hence precise measurement of the volume of the sample. It also will be evident that modifications can be made in the invention without departing from its spirit and purpose. For example, the plunger and micrometer assembly for drawing the solutions into the inner reservoir may be replaced by other known means which will serve to create the desired fluid flow and provide means for measuring the changes in volume of the inner reservoir. Such means may be mechanical, electromechanical, pneumatic or electronic, the objective being to effect the desired displacement of the fluids and measure the volume of the sample as it passes through the capillary tube. Similarly, the size and proportions of the device may be varied depending on factors such as the surface tension, cohesiveness and viscosity of the reagents being used. Enhanced visibiity of the sample bubble as it passes through the capillary tube may be obtained by increasing the wall thickness of the tube. The analyzer also may be used to measure the concentration of a constituent as indicated by an increase in the volume of the sample depending upon the reagents being used.

What is claimed is:

1. A micro fluid analyzer consisting of an elongated transparent analyzer tube having an outer reservoir with an open outer end, a linear capillary tube connected at one end to the inner end of said outer reservoir, and an inner reservoir connected at its inner end to the opposite end of said capillary tube, said reservoirs and said capillary tube lying in tandem relation to each other, displacement means operatively connected to the outer end of said inner reservoir for drawing a carrier fluid placed in the outer reservoir through said capillary tube into the inner reservoir, means for measuring the volume of fluid drawn into the inner reservoir, and reference means in association with said capillary tube for determining the extent of a sample bubble of a fluid to be analyzed which is injected into the carrier fluid in the outer reservoir and drawn through the capillary tube as a concomitant of drawing the carrier fluid into said inner reservoir.

2. The micro fluid analyzer claimed in claim 1 wherein said displacement means comprises a plunger axially displaceable within said inner reservoir.

3. The micro fluid analyzer claimed in claim 2 wherein the means for measuring the volume of fluid drawn into said inner reservoir comprises micrometer means operatively connected to said plunger.

4. The micro fluid analyzer claimed in claim 1 wherein the uppermost inner surfaces of said reservoirs and said capillary tube lie in a common plane.

5. The micro fluid analyzer claimed in claim 1 wherein said displacement means comprises a micrometer assembly including a body secured to the outer end of said inner reservoir, an axially displaceable plunger mounted in said body and positioned to move within said inner reservoir, a rotatable head mounted on said body and operatively connected to said plunger, whereby rotation of said head will displace said plunger, and wherein the means for measuring the volume of fluid in said inner reservoir comprises calibrated indicia on said micrometer assembly for measuring the displacement of said plunger.

6. The micro fluid analyzer claimed in claim 1 including a protective transparent jacket surrounding said analyzer tube.

7. The micro fluid analyzer claimed in claim 6 wherein said jacket is sealed relative to said analyzer tube and is adapted to contain an insulating fluid.

8. The micro fluid analyzer claimed in claim 6 including stabilizing means for said analyzer.

9. The micro fluid analyzer claimed in claim 8 wherein said stabilizing means comprises a supporting platform comprising a seat for said analyzer.

10. The micro fluid analyzer claimed in claim 9 wherein said platform has an inclined surface on which said analyzer is seated.

* * * * *